April 30, 1940. N. GRILLO Plant Pat. 382
ROSE PLANT
Filed April 3, 1939
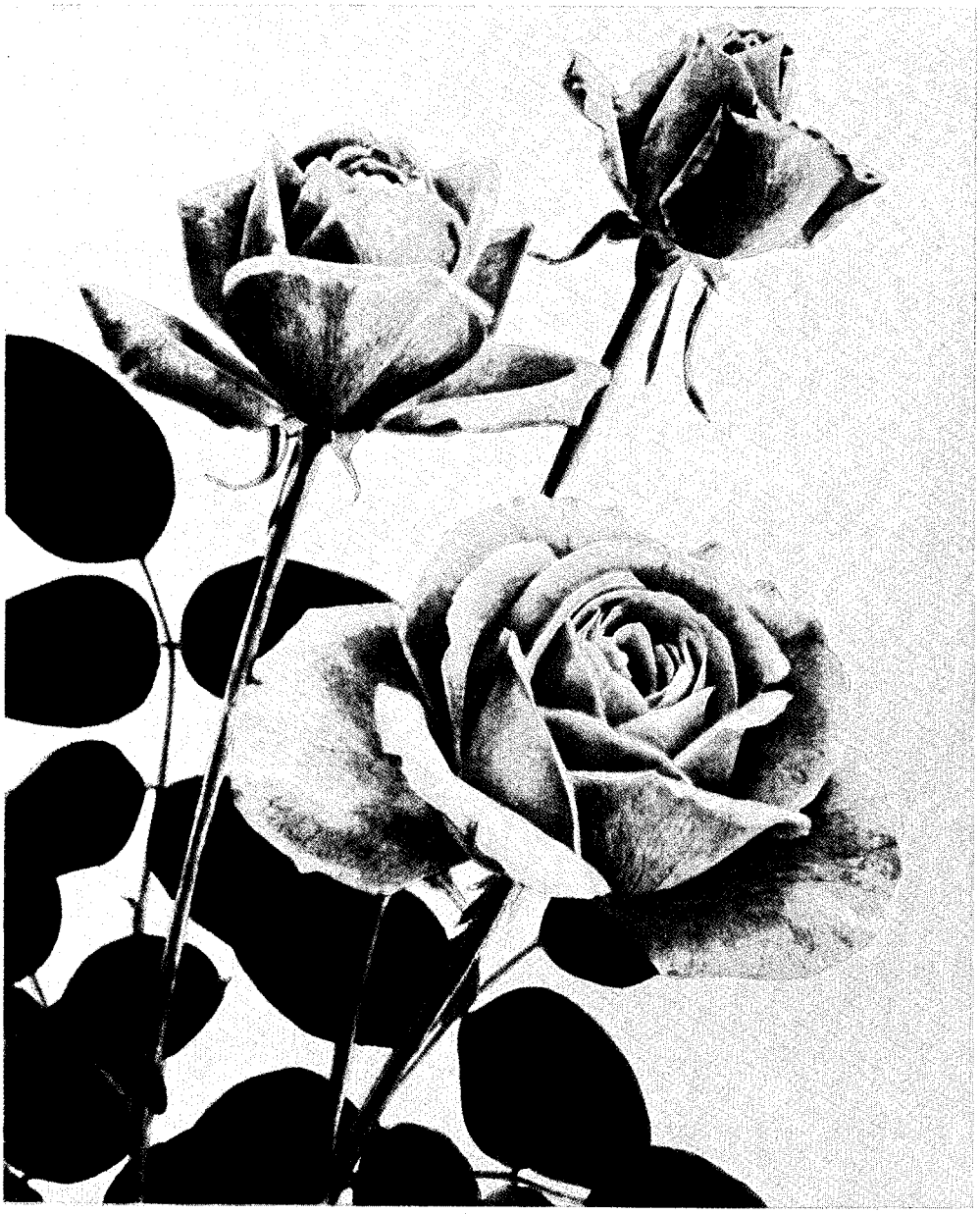
INVENTOR
Nicholas Grillo
By Orville M. Kile
Plant Patent Agent Patented Apr. 30, 1940

Plant Pat. 382

UNITED STATES PATENT OFFICE

382

ROSE PLANT

Nicholas Grillo, Milldale, Conn.

Application April 3, 1939, Serial No. 265,843

1 Claim. (Cl. 47—61)

My new discovery relates to improvements in roses of the hybrid tea class and pertains particularly to red roses.

My new rose is a sport of Better Times, which is the subject of Plant Patent No. 23, and was discovered by me as a branch of the parent plant. It possesses many of the characteristics of its parent, but differs in several important respects.

The most outstanding characteristic of my new rose is its absolute thornlessness. There is no thorn or prickle present on any part of the stem or leaf. So far as I have been able to learn, no other hybrid tea rose exists which is absolutely thornless, although some may have very few thorns and some may have no thorns on the stems but have prickles on other portions of the plant.

The color of my new rose is much darker than that of its parent; the new rose has a greater number of petals; its foliage is smaller and somewhat darker; and its blossom differs in form.

I have asexually reproduced this new variety and its distinguishing characteristics have proved to be firmly fixed.

The original illustrations accompanying these specifications show three specimens of my new rose in various stages of opening, in approximately their true colors.

Reference to color plates indicates Ridgway's Color Standards and Nomenclature. Where no reference is given, the ordinary dictionary term is intended.

Following is a detailed description of this new variety.

*The plant*

Growth habits: Similar to those of its parent, but a little more vigorous and prolific.

Foliage: Abundant; smaller than that of parent.

*Leaflets.*—3 to 5. Color—Dark Dull Yellow Green (Plate XXXII). Seize—medium. Average terminal leaflet measures 2 inches long by 1¼ inches wide. Shape—oval with acuminate apex. Texture—heavy and smooth. Edge—evenly, finely and sharply serrated.

*Rachis.*—Medium size; grooved above; smooth below.

*Stipules.*—Small; clinging; have sharp points which stand almost at right angles.

*Sepals.*—Simple; medium length, averaging approximately 1¼ inches; same colors as stems.

*Thorns.*—Absolutely no thorns or prickles occur.

*Stems.*—Long; slender but adequately strong to hold blossoms erect; approximately Cerro Green (Plate V).

*The flower*

Bud:

*Size.*—Medium.

*Shape.*—Somewhat blunt; shorter than the bud of Better Times.

*Opening.*—Perfect.

*Color.*—There is no color in Ridgway's Color Standards exactly like the color of this bud but Pomegranate Purple (Plate XII) is approximately correct.

Bloom:

*Borne.*—Singly on long stems.

*Size.*—Medium, being 4 inches across.

*Form.*—Full, deep cup-shape, which it retains. Inner petals imbricated and distinct upon opening. As flower ages the outer and intermediate petals roll back at edges but do not distinctly quill.

*Color.*—The color of the open rose is slightly lighter than the bud and would fall between Pomegranate Purple (Plate XII) and Tyrian Rose (Plate XII). This color is rather evenly distributed with the exception of the base of the petal which is lighter, and occasional white stripes are noticed at the center of the inside of some of the petals. As the flower ages the outer petals of the outer row purple slightly, and the inner petals lighten considerably.

*Petalage.*—Average 60 to 65 petals in October, including petaloids. Petals, Shape—nearly round, with only slightly flattened top. Outer petals are considerably bulged. Edges usually somewhat ruffled and notched. Size—medium; 1¾ inches by 1⅝ inches. Texture—heavy. Arrangement—the large outer petals form a deep cup while the inner petals are imbricated.

*Reproductive organs*

Pistils: Many; bunched.

*Stigmas.*—Spinel Pink to Spinel Red (Plate XIII), topped with dot of yellowish white.

*Styles.*—Yellowish white.

Stamens: Few; surround pistils. Petaloids appear to have taken the place of many stamens.

*Anthers.*—Buff-Yellow (Plate IV).

Having thus disclosed my discovery, I claim:

The new variety of hybrid tea rose, substantially as shown and described, characterized particularly by its absolute thornlessness; its medium-sized, dark foliage; and its prolific production of flowers having a very large number of petals and distinctive color falling between Tyrian Rose and Pomegranate Purple.

NICHOLAS GRILLO.